(12) United States Patent
Chen

(10) Patent No.: US 11,624,845 B2
(45) Date of Patent: *Apr. 11, 2023

(54) METHODS AND SYSTEMS FOR CALIBRATING AN X-RAY APPARATUS

(71) Applicant: SHANGHAI UNITED IMAGING HEALTHCARE CO., LTD., Shanghai (CN)

(72) Inventor: Hongwei Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,645

(22) Filed: May 9, 2022

(65) Prior Publication Data
US 2022/0268954 A1 Aug. 25, 2022

Related U.S. Application Data

(63) Continuation of application No. 17/133,527, filed on Dec. 23, 2020, now Pat. No. 11,346,965, which is a
(Continued)

(30) Foreign Application Priority Data

Jun. 29, 2018 (CN) .......................... 201810701031.8

(51) Int. Cl.
*A61B 6/00* (2006.01)
*G01T 7/00* (2006.01)
(Continued)

(52) U.S. Cl.
CPC ................ *G01T 7/005* (2013.01); *A61B 6/06* (2013.01); *A61B 6/4452* (2013.01); *A61B 6/547* (2013.01); *A61B 6/585* (2013.01); *G21K 1/02* (2013.01)

(58) Field of Classification Search
CPC ........ A61B 6/582; A61B 6/547; A61B 6/4452
See application file for complete search history.

(56) References Cited

U.S. PATENT DOCUMENTS 11,346,965 B2 * 5/2022 Chen .................... A61B 6/4452
2004/0105526 A1 6/2004 Zhang et al.
(Continued)

FOREIGN PATENT DOCUMENTS

CN 2570780 Y 9/2003
CN 104207795 A 12/2014
(Continued)

OTHER PUBLICATIONS

International Search Report in PCT/CN2019/094006 dated Aug. 28, 2019, 5 pages.
(Continued)

*Primary Examiner* — Dani Fox
(74) *Attorney, Agent, or Firm* — Metis IP LLC

(57) ABSTRACT

The present disclosure relates to methods and systems for calibrating an X-ray apparatus. The X-ray apparatus may include an X-ray detector and a collimator. To calibrate the X-ray apparatus, the methods and systems may include moving the X-ray detector from a first position to a second position along a first axis of a coordinate system, wherein the first position is under a scanning table, and the second position is outside the scanning table; moving the collimator to align the collimator with the X-ray detector at the second position; determining one or more parameters; and determining a second value of the first encoder when the collimator is aligned with the X-ray detector at the first position based on the one or more parameters.

20 Claims, 7 Drawing Sheets

Related U.S. Application Data continuation of application No. PCT/CN2019/094006, filed on Jun. 29, 2019.

(51) Int. Cl.
*A61B 6/06* (2006.01)
*G21K 1/02* (2006.01)

(56) References Cited

U.S. PATENT DOCUMENTS

| | | |
|---|---|---|
| 2008/0170665 A1 | 7/2008 | Marar et al. |
| 2012/0177171 A1 | 7/2012 | Gutfleisch et al. |
| 2017/0161899 A1 | 6/2017 | Takemoto et al. |
| 2017/0347978 A1* | 12/2017 | Küspert ............... A61B 6/4452 |
| 2018/0085082 A1 | 3/2018 | Kawano |
| 2018/0220989 A9 | 8/2018 | Deinlein et al. |

FOREIGN PATENT DOCUMENTS

| | | |
|---|---|---|
| CN | 104337530 A | 2/2015 |
| CN | 204520731 U | 8/2015 |
| CN | 106773513 A | 5/2017 |
| EP | 0238866 A1 | 9/1987 |
| EP | 2609859 A1 | 7/2013 |
| WO | 2020001654 A1 | 1/2020 |

OTHER PUBLICATIONS

Written Opinion in PCT/CN2019/094006 dated Aug. 28, 2019, 5 pages.
First Office Action in Chinese Application No. 201810701031.8 dated Feb. 28, 2020, 11 pages.
The Extended European Search Report in European Application No. 19824773.6 dated Jul. 15, 2021, 7 pages.

* cited by examiner

METHODS AND SYSTEMS FOR CALIBRATING AN X-RAY APPARATUS

CROSS-REFERENCE TO THE RELATED APPLICATIONS

This present application is a Continuation of U.S. application Ser. No. 17/133,527, filed on Dec. 23, 2020, which a Continuation of International Application No. PCT/CN2019/094006 filed on Jun. 29, 2019, which claims priority of Chinese Application No. 201810701031.8, filed on Jun. 29, 2018, the contents of each of which are hereby incorporated by reference in its entirety.

TECHNICAL FIELD

The present disclosure generally relates to X-ray imaging, and more specifically relates to methods and systems for calibrating an X-ray apparatus.

BACKGROUND

An X-ray imaging system generally allows X-rays emitted by an X-ray source to irradiate an object, and detects X-rays that have transmitted through the object by an X-ray detector. The X-ray imaging systems can easily identify internal structure of the object based on an image generated by the X-ray detector, and diagnose a disease of the object. The X-ray imaging system generally has a collimator for shielding a portion of the X-rays and defining an irradiation region on the object. The collimator is disposed on the X-ray source. In some cases, the X-ray source and the collimator are not fixedly connected with the X-ray detector. The X-ray detector may need to aligned with the collimator to ensure the X-ray detector detects the X-rays transmitted through the object. However, for an decubitus imaging system, it is required to move a bed board of a scanning table outside the scanning table, to align the collimator and X-ray detector installed on the scanning table. The alignment process is cumbersome and inefficient. Thus, it is desirable to provides convenient systems and methods for effectively calibrating the X-ray detector and the collimator.

SUMMARY

In one aspect of the present disclosure, a method for calibrating an X-ray apparatus is provided. The X-ray apparatus may include an X-ray detector and a collimator. The method may include moving the X-ray detector from a first position to a second position along a first axis of a coordinate system. The first position may be under a scanning table, and the second position may be outside the scanning table. The method may also include moving the collimator to align the collimator with the X-ray detector at the second position. The method may include determining one or more parameters. The one or more parameters may include at least one of a distance between the first position and the second position, or a first value of a first encoder of the collimator when the collimator is aligned with the X-ray detector at the second position. The first encoder may detect a movement of the collimator along the first axis of the coordinate system. The method may further include determining a second value of the first encoder when the collimator is aligned with the X-ray detector at the first position based on the distance between the first position and the second position and the first value of the first encoder.

In some embodiments, the moving the collimator to align the collimator with the X-ray detector may include moving the collimator to align a center of a beam field of the collimator with a center of an imaging region of the X-ray detector at the second position.

In some embodiments, the first position may have a first reference coordinate along the first axis and/or a second reference coordinate along a second axis.

In some embodiments, the method may further include moving the X-ray detector back to the first positon; and moving the collimator based on the second value of the first encoder so that the collimator is aligned with the X-ray detector at the first position.

In some embodiments, the collimator may further include a second encoder and a third encoder. The second encoder may detect a movement of the collimator along a second axis of the coordinate system, and the third encoder may detect a movement of the collimator along a third axis of the coordinate system.

In some embodiments, the one or more parameters may further include a value of the second encoder and a value of the third encoder when the collimator is aligned with the X-ray detector at the second position. The moving the collimator so that the collimator is aligned with the X-ray detector at the first position may further include moving the collimator based on the second value of the first encoder, the value of the second encoder, and the value of the third encoder.

In some embodiments, the X-ray detector may include a fourth encoder and a fifth encoder. The fourth encoder may detect a movement of the X-ray detector along a second axis of the coordinate system, and the fifth encoder may detect a movement of the X-ray detector along a third axis of the coordinate system.

In some embodiments, the one or more parameters may further include a value of the fourth encoder and a value of the fifth encoder when the X-ray detector at the second position. The value of the fourth encoder may correspond to a second reference coordinate of the X-ray detector along the second axis, and the value of the fifth encoder may correspond to a third reference coordinate of the X-ray detector along the third axis.

In some embodiments, the X-ray detector further includes a sixth encoder, wherein the sixth encoder detects a movement of the X-ray detector along the first axis of the coordinate system and detects a coordinate of the second position of the X-ray detector along the first axis.

In some embodiments, the determining a second value of the first encoder may include determining the second value of the first encoder based on the first value of the first encoder, a coefficient of the first encoder, and the distance between the first position and the second position.

In some embodiments, the collimator and the X-ray detector may be aligned periodically.

In another aspect of the present disclosure, a system for calibrating an X-ray apparatus is provided. The X-ray apparatus may include an X-ray detector and a collimator. The system may include at least one storage device including a set of instructions; and at least one processor in communication with the at least one storage device. When executing the set of instructions, the at least one processor may be configured to cause the system to move the X-ray detector from a first position to a second position along a first axis of a coordinate system. The first position may be under a scanning table, and the second position may be outside the scanning table. The at least one processor may also be configured to move the collimator to align the collimator with the X-ray detector at the second position; and determine one or more parameters. The one or more parameters may include at least one of a distance between the first position and the second position, or a first value of a first encoder of the collimator when the collimator is aligned with the X-ray detector at the second position. The first encoder may detect a movement of the collimator along the first axis of the coordinate system. The at least one processor may further be configured to determine a second value of the first encoder when the collimator is aligned with the X-ray detector at the first position based on the distance between the first position and the second position and the first value of the first encoder.

In yet another aspect of the present disclosure, a non-transitory computer-readable medium is provided. The non-transitory computer-readable medium may include at least one set of instructions. When executed by at least one processor of a computing device, the at least one set of instructions may cause the at least one processor to effectuate a method including moving the X-ray detector from a first position to a second position along a first axis of a coordinate system, wherein the first position is under a scanning table, and the second position is outside the scanning table; moving the collimator to align the collimator with the X-ray detector at the second position; determining one or more parameters, wherein the one or more parameters include at least one of a distance between the first position and the second position, or a first value of a first encoder of the collimator when the collimator is aligned with the X-ray detector at the second position, wherein the first encoder detects a movement of the collimator along the first axis of the coordinate system; and determining a second value of the first encoder when the collimator is aligned with the X-ray detector at the first position based on the distance between the first position and the second position and the first value of the first encoder.

In yet another aspect of the present disclosure, an X-ray imaging system is provided. The X-ray imaging system may include an X-ray apparatus and a computing device. The computing device may include a processor, and a storage medium storing computer programs. When executing the computer programs, the processor may be configured to perform the method for calibrating an X-ray apparatus of any one of claims 1-9.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
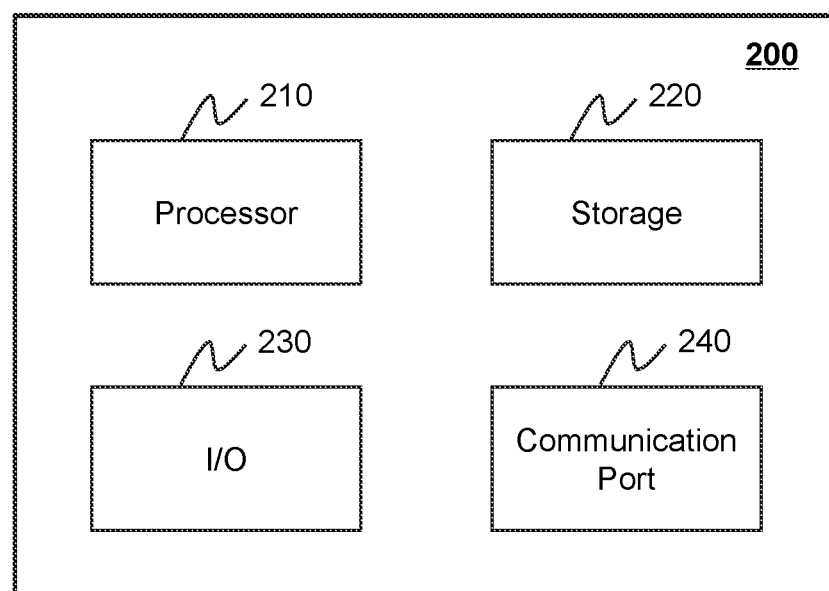
FIG. 2 is a schematic diagram illustrating exemplary hardware and/or software components of a computing device on which the processing device may be implemented according to some embodiments of the present disclosure.

Generally, the word "module," "unit," or "block," as used herein, unless otherwise defined, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for calibrating an X-ray apparatus. The X-ray apparatus may include an X-ray detector and a collimator. The systems and methods may be configured to calibrate and/or align the X-ray detector and the collimator. Specifically, the systems and methods may move the X-ray detector from a first position to a second position along a first axis of a coordinate system. The first position may be under a scanning table, and the second position may be outside the scanning table. The systems and methods may move the collimator to align the collimator with the X-ray detector at the second position. For example, the systems and methods may move the collimator to align a center of a beam field of the collimator with a center of an imaging region of the X-ray detector at the second position. When the collimator is aligned with the X-ray detector at the second position, the systems and methods may determine one or more parameters. The one or more parameters may include a distance between the first position and the second position, a first value of a first encoder of the collimator, or the like. The systems and methods may further determine a second value of the first encoder when the collimator is aligned with the X-ray detector at the first position based on the distance between the first position and the second position and the first value of the first encoder.

Figure 1:
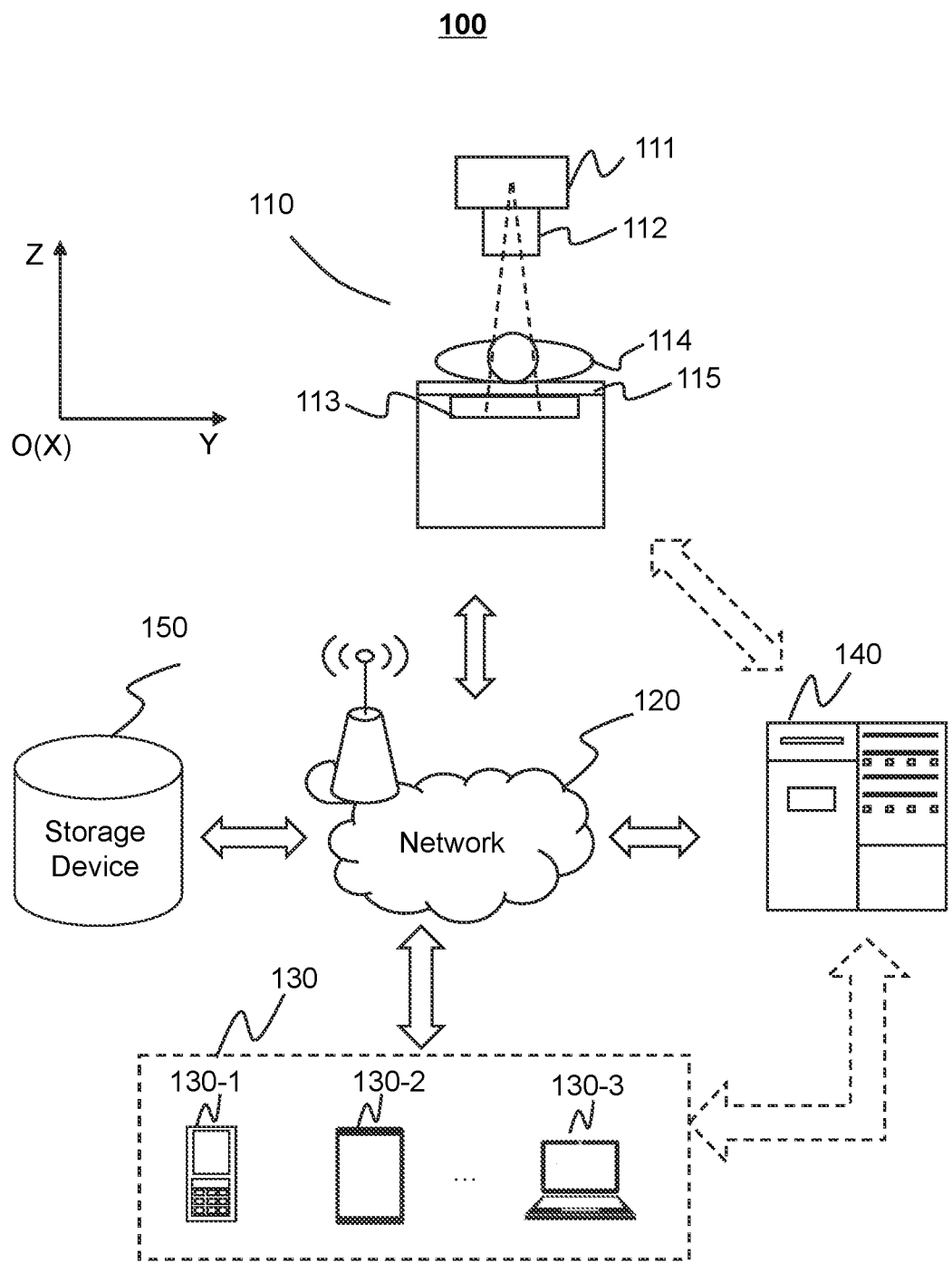
FIG. 1 is a schematic diagram illustrating an exemplary X-ray imaging system according to some embodiments of the present disclosure.

FIG. 1 is a schematic diagram illustrating an exemplary X-ray imaging system according to some embodiments of the present disclosure. The X-ray imaging system 100 may include an X-ray apparatus 110, a network 120, one or more terminals 130, a processing device 140, and a storage device 150. The components of the X-ray imaging system 100 may be connected in various ways. Merely by way of example, the X-ray apparatus 110 may be connected to the processing device 140 through the network 120. As another example, the X-ray apparatus 110 may be connected to the processing device 140 directly as indicated by the bi-directional arrow in dotted lines linking the X-ray apparatus 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the X-ray apparatus 100 may be a decubitus imaging apparatus. As shown in FIG. 1, the X-ray apparatus 110 may include an X-ray source 111, a collimator 112, an X-ray detector 113, and a scanning table 115. The X-ray source 111 may be configured to emit X-rays toward an object (e.g., the object 114). The object may be a biological object (e.g., a patient, an animal) or a non-biological object (e.g., a human-made object). In the present disclosure, "object" and "subject" are used interchangeably. The X-ray detector 113 may be disposed opposite to the X-ray source 111 for detecting X-rays transmitted through the object and generating X-ray images. In some embodiments, the X-ray detector 113 may include a plurality of detector units. The detector units may include a scintillation detector (e.g., a cesium iodide detector) or a gas detector. The detector units may be arranged in a single row or multiple rows. The collimator 112 may be disposed on an X-ray emitting side of the X-ray source 111. The collimator 112 may be configured to guide a path of the X-rays emitted from the X-ray source 111 and adjust an irradiation region irradiated by the X-rays. Merely by way of example, the collimator 112 may have four leaves (not shown in FIG. 1). These four leaves may be arranged to shield a portion of the X-rays emitted from the X-ray source 111 and restrict the X-rays to irradiate a rectangular area of arbitrary size (e.g., 10*10, 10*15, 20*20, 30*40, 43*43).

Figure 6:
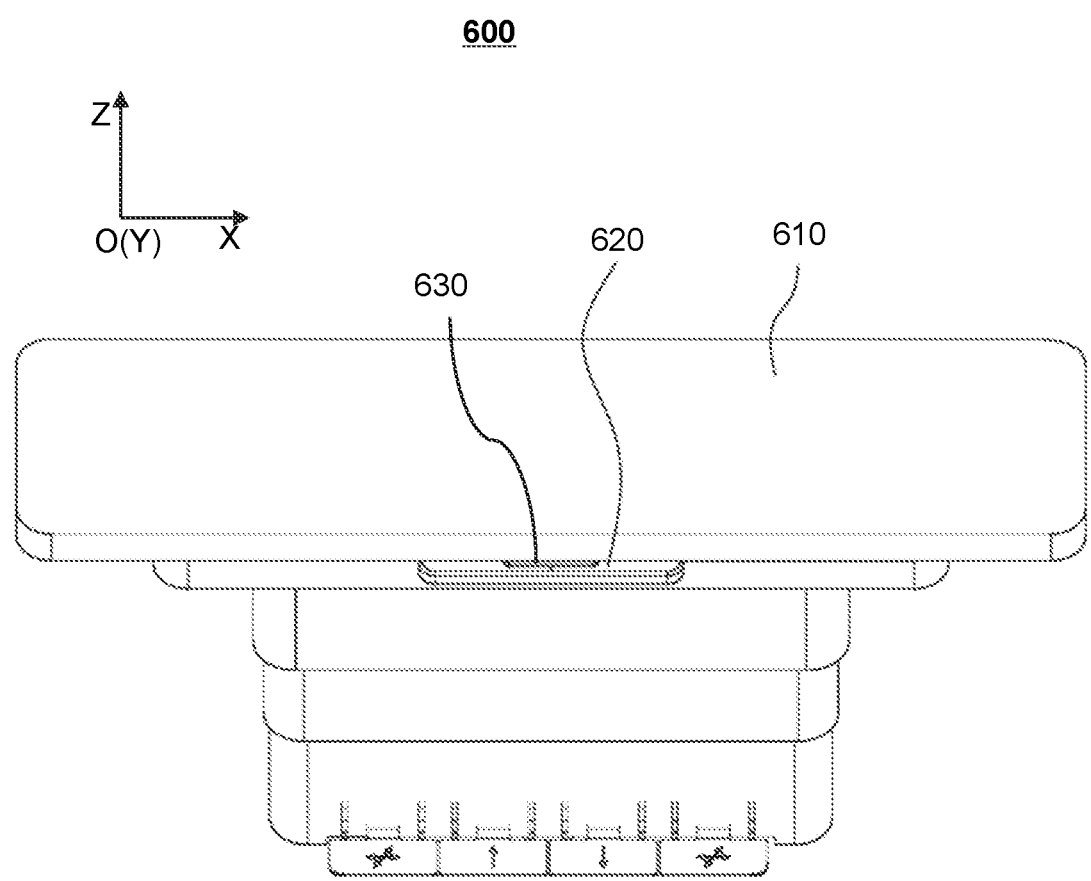
FIG. 6 is a schematic diagram illustrating a portion of an exemplary X-ray apparatus according to some embodiments of the present disclosure.
Figure 7:
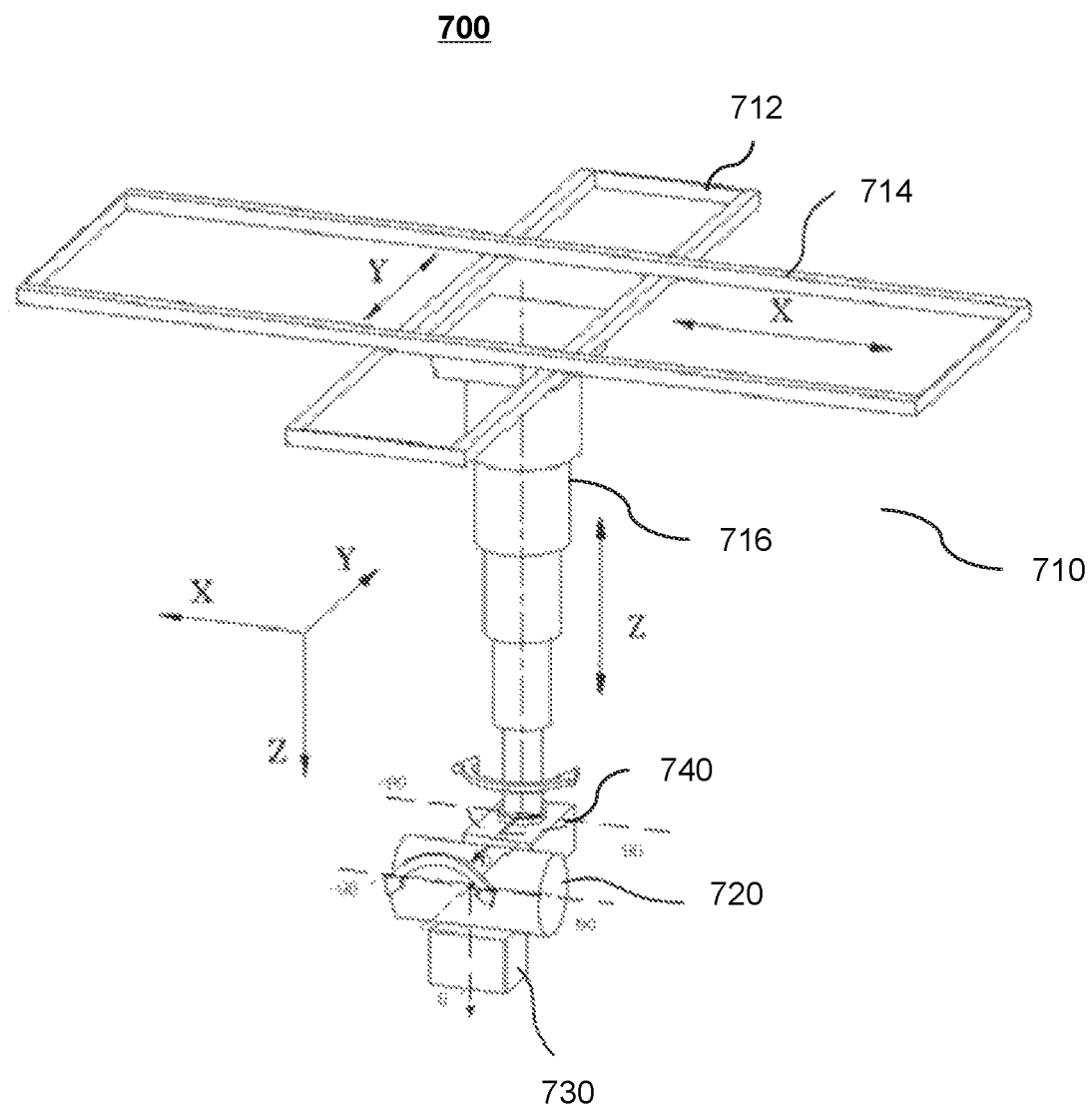
FIG. 7 is a schematic diagram illustrating a portion of an exemplary X-ray apparatus according to some embodiments of the present disclosure.

For illustration purposes, a coordinate system as shown in FIG. 1 is introduced. The coordinate system may include an X-axis, a Y-axis, and a Z-axis. The Z-axis may refer to a direction perpendicular to the scanning table (e.g., perpendicular to a horizontal plane). The X-axis may refer to a long axis of the scanning table. The Y-axis may refer to a short axis of the scanning table. The collimator 112 may be connected to the X-ray source, and thus, the collimator 112 may move to accompany the X-ray source 111. That is, the collimator 113 may be movable with the X-ray source 111 collectively. In some embodiments, the X-ray source 111 and the collimator 112 may be disposed on a support component (e.g., the support component 710 as illustrated in FIG. 7). In some embodiments, the X-ray detector 113 may be disposed under the scanning table 115 via a tray (e.g., the tray 620 as illustrated in FIG. 6). Since the X-ray source 111 (or the collimator 112) is not fixedly connected with the X-ray detector 113, the X-ray detector 113 and the X-ray source 111 (or the collimator 112) may need to be aligned with each other to ensure the X-ray detector 113 detects X-rays transmitted through the object. During an X-ray imaging process, the X-ray detector 113 may move along at least one of the X-axis, the Y-axis, or the Z-axis. For example, the X-ray detector 113 may move along the X-axis. The X-ray source 111 (or the collimator 112) may move along at least one of the X-axis, the Y-axis, or the Z-axis independently of the X-ray detector 113. However, to ensure the X-ray detector 113 is aligned with the X-ray source 111 (or the collimator 112), the X-ray source 111 (or the collimator 112) and the X-ray detector 113 may need to move simultaneously or synchronously.

The network 120 may facilitate the exchange of information and/or data. In some embodiments, one or more components of the X-ray imaging system 100 (e.g., the X-ray apparatus 110, the terminal 130, the processing device 140, or the storage device 150) may send information and/or data to another component(s) in the X-ray imaging system 100 via the network 120. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the radiation system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the X-ray apparatus 110. In some embodiments, the terminal 130 may operate the X-ray apparatus 110 via a wireless connection. In some embodiments, the terminal 130 may receive information and/or instructions inputted by a user, and send the received information and/or instructions to the X-ray apparatus 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the X-ray apparatus 110, the terminal 130, or the storage device 150. For example, the processing device 140 may move a collimator to align the collimator with an X-ray detector at the second position. The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the X-ray apparatus 110, the terminal 130, and/or the storage device 150 via the network 120. As another example, the processing device 140 may be directly connected to the X-ray apparatus 110 (as illustrated by the dashed bidirectional arrow linking the X-ray apparatus 110 and the processing device 140 in FIG. 1), the terminal 130 (as illustrated by the dashed bidirectional arrow linking the terminal 130 and the processing device 140 in FIG. 1), and/or the storage device 150, to access information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation system 100 (e.g., the terminal 130, the processing device 140). One or more components of the radiation system 100 may access the data or instructions stored in the storage device 150 via the network 120. In some embodiments, the storage device 150 may be directly connected to or communicate with one or more components of the radiation system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the X-ray apparatus 110, the terminal 130, the storage device 150, and/or any other component of the radiation system 100. For example, the processor 210 may move a collimator to align the collimator with the X-ray detector at the second position. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the X-ray apparatus 110, the terminal 130, the storage device 150, or any other component of the radiation system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the X-ray apparatus 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
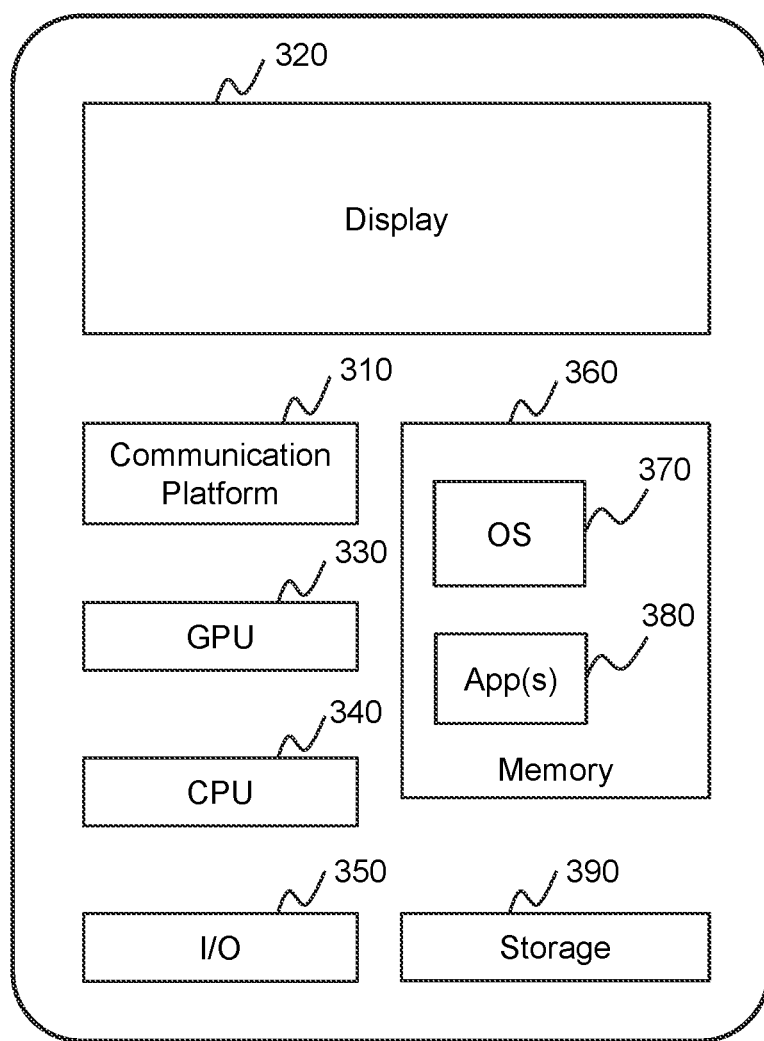
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the X-ray imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to align a collimator with an X-ray detector as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
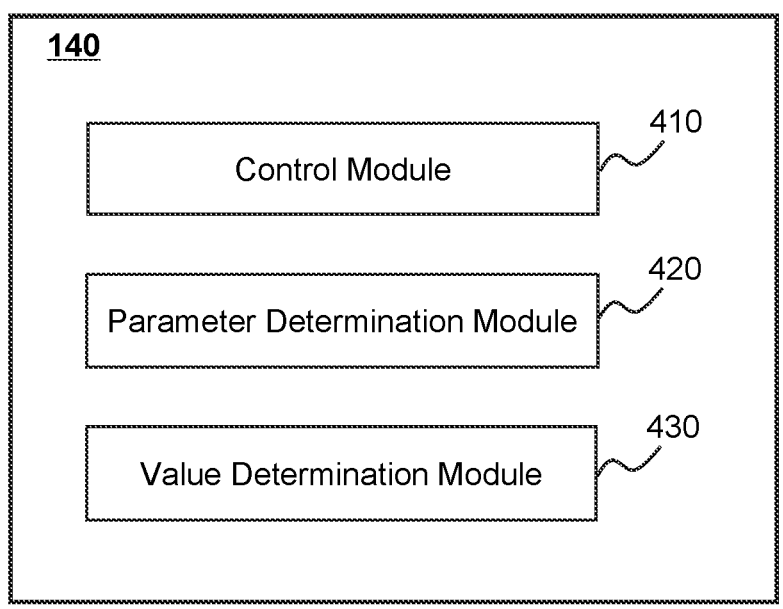
FIG. 4 is a schematic diagram illustrating an exemplary processing device according to some embodiments of the present disclosure.

FIG. 4 is a block diagram illustrating an exemplary processing device 140 according to some embodiments of the present disclosure. The processing device 140 may be implemented on the computing device 200 (e.g., the processor 210) as illustrated in FIG. 2 or the CPU 340 as illustrated in FIG. 3. The processing device 140 may include a control module 410, a parameter determination module 420, and a value determination module 430.

The control module 410 may be configured to control the movement of one or more components of the X-ray imaging system 100. In some embodiments, the control module 140 may move the X-ray detector from a first position to a second position along a first axis of a coordinate system (e.g., the Y-axis of the coordinate system as illustrated in FIG. 1). The first position may be under a scanning table, and the second position may be outside the scanning table. The control module 410 may also move a collimator to align the collimator with the X-ray detector at the second position. Specifically, the control module 410 may move the collimator to align a center of a beam field of the collimator with a center of an imaging region of the X-ray detector at the second position. When the collimator is aligned with the X-ray detector, the control module 410 may move the X-ray detector back to the first position. The control module 410 may also move the collimator so that the collimator is aligned with the X-ray detector at the first position. In some embodiments, the X-ray detector may be moved from the first position to the second position manually. For example, the X-ray detector may be moved from the first position to the second position by manually pulling the tray out of the scanning table by a user. Correspondingly, the X-ray detector may be moved back to the first position manually. For example, the X-ray detector may be moved from the second position back to the first position by manually pushing the tray in the scanning table by the user.

The parameter determination module 420 may be configured to determine one or more parameters. The one or more parameters may include a distance between the first position and the second position, a first value of a first encoder of the collimator when the collimator is aligned with the X-ray detector at the second position, or the like. In some embodiments, the one or more parameters may further include a value of a second encoder, a value of a third encoder when the collimator is aligned with the X-ray detector at the second position. The first encoder may be used to detect a movement of the collimator along the first axis. The second encoder may be used to detect a movement of the collimator along a second axis of the coordinate system (e.g., the X-axis of the coordinate system as illustrated in FIG. 1). The third encoder may be used to detect a movement of the collimator along a third axis of the coordinate system (e.g., the Z-axis of the coordinate system as illustrated in FIG. 1).

The value determination module 430 may be configured to determine a second value of the first encoder when the collimator is aligned with the X-ray detector at the first position based on the one or more parameters. Merely by way of example, the value determination module 430 may determine the second value of the first encoder based on the first value of the first encoder, a coefficient of the first encoder, and the distance between the first position and the second position.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, any one of the modules may be divided into two or more units. For example, the control 410 may be divided into a first control unit and a second control unit. The first control unit may be configured to control the movement of the X-ray detector, and the second control unit may be configured to control the movement of the collimator. In some embodiments, the processing device 140 may include one or more additional modules. For example, the processing device 140 may include a storage module (not shown). The storage module may be configured to store data generated during any process performed by any component of the processing device 140.

Figure 5:
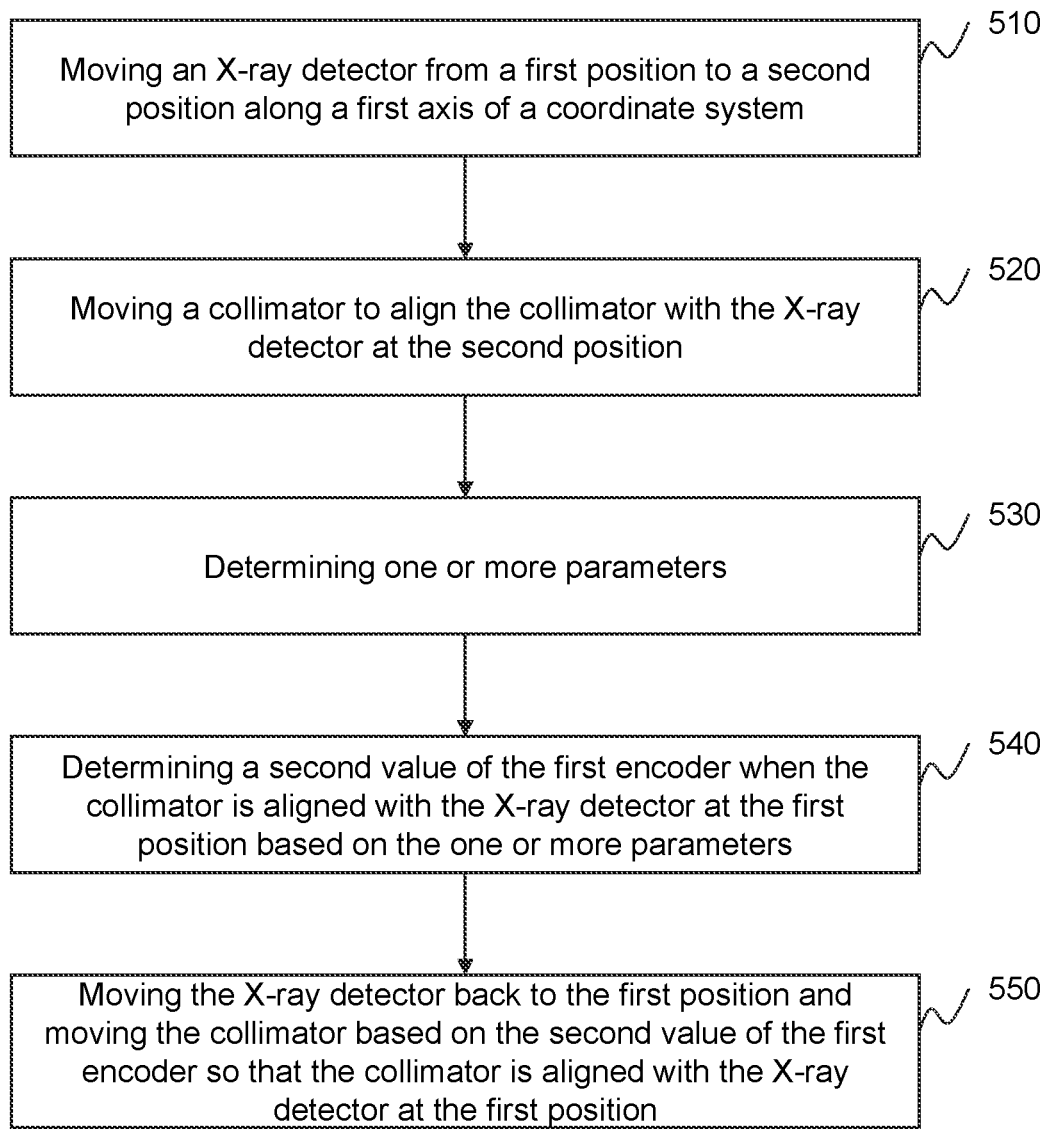
FIG. 5 is a flowchart illustrating an exemplary process for calibrating an X-ray apparatus according to some embodiments of the present disclosure.

FIG. 5 is a flowchart illustrating an exemplary process 500 for calibrating an X-ray apparatus according to some embodiments of the present disclosure. In some embodiments, the X-ray apparatus may be a decubitus imaging apparatus. In some embodiments, the X-ray apparatus may include an X-ray detector and a collimator. The process 500 may be used to calibrate and/or align the X-ray detector and the collimator. The process 500 may be implemented in the X-ray imaging system 100 illustrated in FIG. 1. For example, the process 500 may be stored in the storage device 150 and/or the storage 220 in the form of instructions (e.g., an application), and invoked and/or executed by the processing device 140 (e.g., the processor 210 illustrated in FIG. 2, the CPU 340 as illustrated in FIG. 3, or one or more modules in the processing device 140 illustrated in FIG. 10). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 140 (e.g., the control module 410) may move the X-ray detector (e.g., the X-ray detector 113) from a first position to a second position along a first axis of a coordinate system (e.g., the Y-axis of the coordinate system as illustrated in FIG. 1). In some embodiments, the first position may be under the scanning table (e.g., the scanning table 115), and the second position may be outside the scanning table. In some embodiments, the first position and/or the second position may indicate position(s) at which a center of an imaging region of the X-ray detector locates. In some embodiments, the first position may also be referred to as a reference position. In some embodiments, the reference position may be a position on the scanning table. Preferably, the reference position may be a center of a bed board of the scanning table. The reference position may be generally regarded as a reference point to determine the first position of the X-ray detector. When the X-ray detector is located at the second position, the center of the imaging region of the X-ray detector may not be shielded by the scanning table. The second position may be determined when the scanning table is fabricated. For example, the X-ray detector is disposed on a tray under the scanning table. The tray may move out of the scanning table along the first axis. The second position may be determined based on a distance that the tray can move along the first axis. Alternatively, the second position may be a position having a first predetermined distance from the first position along the first axis. The first predetermined distance may be a default value or an empirical value related to the X-ray imaging system 100. The first predetermined distance may be any value as long as the center of the imaging region of the X-ray detector is not shielded by the scanning table at the second position. In some embodiments, the second position may also be referred to as a correction position. In some embodiments, the X-ray detector may be moved from the first position to the second position by the processing device 140 (e.g., the control module 410). Alternatively, the X-ray detector may be moved from the first position to the second position manually. For example, the X-ray detector may be moved by pulling the tray out of the scanning table by a user.

In some embodiments, the first position may be regarded as a reference position of the X-ray apparatus that is used to align the X-ray detector and the collimator. The reference position may be selected as a center of the bed board of the scanning table. Generally, the reference position may be designated as a coordinate origin of the coordinate system (e.g., the coordinate system as illustrated in FIG. 1). The reference position (or the coordinate origin) may be used to as a point of reference for space changes of the positions of the X-ray detector and/or the collimator in subsequent use (e.g., performing an X-ray scanning). In prior art, when the X-ray detector and the collimator are calibrated, the X-ray detector may need to move to the coordinate origin (i.e., the reference position). The collimator and the X-ray detector are calibrated at the coordinate origin to obtain one or more parameters related to the X-ray detector and/or the collimator. In the present disclosure, it is not necessary to move the X-ray detector to the reference position, and the X-ray detector may be moved out of the center of the scanning table for calibration. After the one or more parameters at the correction position (i.e., the second position) are determined, the parameters at the reference position (i.e., the first position) may be determined accordingly. Then any component of the X-ray apparatus (e.g., the X-ray detector, the collimator) may be moved to any specified position during the X-ray imaging.

In some embodiments, before operation 501, the processing device 140 may move the X-ray detector to the first position. The X-ray detector may be disposed under the scanning table. In some embodiments, the X-ray detector may be connected with the scanning table directly or indirectly. For example, the X-ray detector may be connected with the scanning table via a tray (e.g., the tray 620 as illustrated in FIG. 6). In some embodiments, the X-ray detector may be movable with respect to the scanning table along at least one of the first axis, a second axis (e.g., the X-axis of the coordinate system as illustrated in FIG. 1), or a third axis (e.g., the Z-axis of the coordinate system as illustrated in FIG. 1).

In some embodiments, the X-ray detector may be fixed to the scanning table along the third axis. The first position may have a first reference coordinate along the first axis and/or a second reference coordinate along the second axis. Before operation 501, the processing device 140 may move the X-ray detector to the first position. Specifically, the processing device 140 may move the X-ray detector along the first axis to the first reference coordinate, and then move the X-ray detector along the second axis to the second reference coordinate. Alternatively, the processing device 140 may move the X-ray detector along the second axis to the second reference coordinate, and then move the X-ray detector along the first axis to the first reference coordinate. Alternatively, the processing device 140 may move the X-ray detector along the first axis and the second axis simultaneously to the first position (e.g., the first reference coordinate and the second reference coordinate). It should be noted that, for the purposes of convenience, the first reference coordinate along the first axis and the second reference coordinate along the second axis may coincide at a horizontal plane that has a predetermined height from the ground, for example, at a center of the bed board of the scanning table. Since the X-ray detector is fixed with respect to the scanning table along the third axis, the X-ray detector may move along the third axis as the scanning table moves up and down. That is, the X-ray detector may move to a predetermined height (also referred to as a third reference coordinate) relative to the ground by controlling the movement of the scanning table. In some embodiments, the predetermined height may be a default value or an empirical value related to the X-ray imaging system 100. The predetermined height may be set according to a default setting of the X-ray imaging system 100, or preset or adjusted by a user. For example, the predetermined height may be a fixed height such as 50 cm, 60 cm, 70 cm, which is convenient for a patient to lie on the scanning table. It should be noted that the X-ray detector may be movable with respect to the scanning table along the third axis, and the X-ray detector may move to the predetermined height by controlling, e.g., by the processing device 140, the movement of the X-ray detector.

In 520, the processing device 140 (e.g., the control module 420) may move the collimator (e.g., the collimator 112) to align the collimator with the X-ray detector at the second position. In some embodiments, the processing device 140 may move the collimator to align a center of a beam field of the collimator with a center of an imaging region of the X-ray detector at the second position. When the collimator is aligned with the X-ray detector, the position of the collimator may be referred to as a correction position of the collimator, which may be recorded by one or more encoders. In some embodiments, the collimator may include a first encoder, a second encoder, and a third encoder. The first encoder may be used to detect a movement of the collimator along the first axis. The second encoder may be used to detect a movement of the collimator along the second axis. The third encoder may be used to detect a movement of the collimator along the third axis. Correspondingly, the X-ray detector may include a fourth encoder and a fifth encoder. The fourth encoder may be used to detect a movement of the X-ray detector along the second axis. The fifth encoder may be used to detect a movement of the X-ray detector along the third axis. In some embodiments, the encoders may be absolute encoders configured to determine absolute positions of the X-ray detector or the collimator. It should be noted that the encoders may be relative encoders configured to determine relative positions (e.g., changes of position) of the X-ray detector or the collimator. In some embodiments, the positions of the X-ray detector or the collimator may be detected by other position sensor, such as a Hall sensor. In some embodiments, the encoders may be the same. Alternatively, at least two of the encoders may be different. For example, the first encoder may be an absolute encoder, while the third encoder may be a relative encoder.

In some embodiments, when performing X-ray imaging, the collimator and the X-ray detector may have a second predetermined distance along the third axis (i.e., the vertical direction). The second predetermined distance may be a default value or an empirical value related to the X-ray imaging system 100. The second predetermined distance may be set according to a default setting of the X-ray imaging system 100, or preset or adjusted by a user. In some embodiments, the second predetermined distance may be a distance value, such as 50 cm, 80 cm, 100 cm, 120 cm, 150 cm, or the like. Preferably, the second predetermined distance may be 100 cm. Alternatively, the second predetermined distance may be a distance range, such as 50-70 cm, 80-120 cm, 100-150 cm, or the like. Preferably, the second predetermined distance may be 80-120 cm. As described in connection with operation 510, the X-ray detector may be located at the predetermined height (e.g., 60 cm relative to the ground). Thus, before the alignment, the collimator may move to a certain coordinate (or a certain height) along the third axis based on the second predetermined distance and the predetermined height. For example, the collimator may move along the third axis to the height of 160 cm relative to the ground.

The beam field of the collimator may have a first crosshair, and the imaging region of the X-ray detector may include a second crosshair. When performing the alignment of the collimator and the X-ray detector, a light source (e.g., a laser light) within the collimator may emit a beam of light. The beam of light may pass through the first crosshair of the beam field to reach the X-ray detector. The first crosshair may have a projection on the X-ray detector. The processing device 140 may move the collimator to align the projection of the first crosshair on the X-ray detector and the second crosshair of the X-ray detector. When the projection of the first crosshair on the X-ray detector is aligned with the second crosshair of the X-ray detector, the collimator and the X-ray detector are aligned.

In 530, the processing device 140 (e.g., the parameter determination module 420) may determine one or more parameters. The one or more parameters may include a distance between the first position and the second position, a first value of the first encoder of the collimator when the collimator is aligned with the X-ray detector at the second position. In some embodiments, the one or more parameters may further include a value of the second encoder and a value of the third encoder when the collimator is aligned with the X-ray detector at the second position. When the collimator and the X-ray detector are aligned, the first value of the first encoder, the value of the second encoder, and/or the value of the third encoder may be directly read. The first value of the first encoder at the second position may correspond to a coordinate of the collimator along the first axis at the second position. The value of the second encoder at the second position may correspond to a coordinate of the collimator along the second axis at the second position. The value of the third encoder at the second position may correspond to a coordinate of the collimator along the second axis at the second position.

In some embodiments, the distance between the first position and the second position may be known. For example, the distance between the first position and the second position may be a distance that the tray (e.g., the tray 620) can move along the first axis, which is determined when the scanning table is fabricated. Alternatively, the X-ray detector may include a sixth encoder, which is used to detect the movement of the X-ray detector along the first axis. For example, the sixth encoder may detect the first reference coordinate of the first position of the X-ray detector along the first axis, and detect a first correction coordinate of the second position of the X-ray detector along the first axis. The value of the sixth encoder at the first position may correspond to the first reference coordinate, and the value of the sixth encoder at the second position may correspond to the first correction coordinate. Then, the distance between the first position and the second position may be determined based on first reference coordinate and the first correction coordinate. The changes of the coordinates of the X-ray detector along the first axis may be represented by the changes of the values of the sixth encoder. Merely by way of example, the distance may be determined according to Equation (1) as below:

$$y = \frac{E'_6 - E_6}{k_6}, \tag{1}$$

wherein y refers to the distance between the first position and the second position; $E_6'$ refers to the value of the sixth encoder at the second position; $E_6$ refers to the value of the sixth encoder at the first position; $k_6$ refers to a coefficient of the sixth encoder.

The one or more parameters may also include a value of the fourth encoder and a value of the fifth encoder when the X-ray detector at the second position. When the processing device 140 moves the X-ray detector from the first position to the second position or from the second position to the first position, the coordinates of the X-ray detector along the second axis and the third axis may be unchanged. That is, the value of the fourth encoder and/or the value of the fifth encoder may be unchanged. The value of the fourth encoder and/or the value of the fifth encoder may be directly read. The value of the fourth encoder may correspond to the second reference coordinate of the X-ray detector along the second axis. Merely by way of example, the first position may be a center of the scanning table, the value of the fourth encoder may be denoted as 0. It should be noted that the fourth encoder may have other values, e.g., a positive value, a negative value. The value of the fifth encoder may correspond to the third reference coordinate of the X-ray detector along the third axis. It should be noted that the value of the encoder (e.g., the fourth encoder, the fifth encoder) may be different from the corresponding coordinate of the X-ray detector. For example, when the height of the X-ray detector is 60 cm, the coordinate along the third axis may be denoted as 600, while the value of the fifth encoder may be denoted as 300.

In some embodiments, the X-ray detector may move along the second axis (e.g., the X-axis). Therefore, it is necessary to calibrate the X-ray detector along the second axis (e.g., the X-axis) of the X-ray detector. In some embodiments, the scanning table may have a marker line along a longitudinal direction of the scanning table (e.g., the X-axis). In some embodiments, the marker line may be a center line along the longitudinal direction of the scanning table. The first position and the second position of the X-ray detector may be configured to align with the marker line. Thus, when the X-ray detector at the second position, the value of the fourth encoder of the X-ray detector may be determined as a reference value. For example, the reference value may correspond to the value of the fourth encoder when the coordinate of the second axis (e.g., the X-axis) is 0. It should be noted that the marker line may not be the center line along the longitudinal direction of the scanning table.

In 540, the processing device 140 (e.g., the value determination module 430) may determine a second value of the first encoder when the collimator is aligned with the X-ray detector at the first position based on the one or more parameters. In some embodiments, the processing device 140 may determine the second value of the first encoder based on the first value of the first encoder, a coefficient of the first encoder, and the distance between the first position and the second position.

In some embodiments, the values of the first encoder and a movement distance of the collimator along the first axis may satisfy Equation (2) as below:

$$E_1 = E_1' + K \times y, \qquad (2)$$

wherein $E_1$ refers to the value of the first encoder after the movement; $E_1'$ refers to the value of the first encoder before the movement; K refers to the coefficient of the first encoder; and y refers to the movement distance of the collimator along the first axis. Thus, the movement distance of the collimator along the first axis and the value difference may satisfy Equation (3) as below:

$$\Delta E = K \times y, \qquad (3)$$

wherein $\Delta E$ refers to the value difference of the first encoder after the movement and be form the movement.

In some embodiments, the processing device 140 may determine the second value of the first encoder according to Equation (4) as below:

$$E_{y1} = E_{y1}' + K \times S, \qquad (4)$$

wherein $E_{y1}$ refers to the second value of the first encoder at the first position; $E_{y1}'$ refers to the first value of the first encoder at the second position; and S refers to the distance between the first position and the second position at which the X-ray detector moves along the Y-axis.

In 550, the processing device 140 (e.g., the control module 410) may move the X-ray detector back to the first position. When the processing device 140 moves the X-ray detector back to the first position, the coordinates of the X-ray detector along the second axis and the third axis may be unchanged. That is, the value of the fourth encoder and/or the value of the fifth encoder may be unchanged. The processing device 140 may also move the collimator based on the second value of the first encoder so that the collimator is aligned with the X-ray detector at the first position. In some embodiments, the processing device 140 may move the collimator based on the second value of the first encoder, the value of the second encoder, and the value of the third encoder. The coordinates of the collimator along the second axis and the third axis may be unchanged, and thus, the value of the second encoder and/or the value of the third encoder may be unchanged. That is, the processing device 140 may move the collimator along the Y-axis. The changes of the coordinates of the collimator along the first axis may be represented by the changes of the values of the sixth encoder. The processing device 140 may move the collimator based on the second value of the first encoder. At the first position, the coordinates of the collimator along the first axis and the second axis may be the same as the coordinates of the X-ray detector along the first axis and the second axis. The coordinate of the collimator along the third axis may be different from the coordinate of the X-ray detector along the third axis. In some embodiments, the height of the collimator may be 160 cm from the ground, and the height of the X-ray detector may be 60 cm from the ground. In some embodiments, when the collimator moves on the plane 160 cm above the ground, i.e., 100 cm above the X-ray detector, the value of the second and third encoders, associated with the X-axis and the Z-axis, of the collimator are designated as the value of these encoders for the collimator aligned with the X-ray detector at the first position. For example, the value of the second encoder may correspond to the coordinate value 0 of the second axis. The value of the third encoder may correspond to the coordinate value 160 of the third axis. The value of the first encoder, associated with the Y-axis, of the collimator when the collimator is aligned with the X-ray detector at the first position may be determined according to Equation (4), which is not repeated herein.

When the collimator is aligned with the X-ray detector at the first position, the X-ray apparatus can be used to perform X-ray imaging. Before performing the X-ray imaging, an imaging protocol may be generated by a doctor. The imaging protocol may include an acquisition protocol and/or a reconstruction protocol. The acquisition protocol may include information relating to a voltage of a tube of an X-ray source (e.g., the X-ray source 111), a current of the tube of the X-ray source, the type of a focal spot of the X-ray source, a size of the focal spot of the X-ray source, a shot number of the X-ray source, a collimation width of the collimator (e.g., the collimator 112), a view number of the X-ray detector (e.g., the X-ray detector 113), one or more body parts to be scanned, a movement direction of the scanning table (e.g., the scanning table 115), position information of the object (e.g., a supine position, a prone position, a decubitus right position, a decubitus left position, etc.), a scanning mode, or the like, or any combination thereof. The reconstruction protocol may include information relating to a reconstruction center, a reconstruction field of view, an intensity viewing window level, an intensity viewing window width, an image thickness, an image increment, an image resolution, a noise level of the image, or the like, or any combination thereof.

One or more parameters may be generated based on the imaging protocol. The one or more parameters may include coordinates of the X-ray detector and/or the collimator along the first axis, the second axis, and the third axis at a target position. The coordinates of the X-ray detector at the target position may be represented by the values of the encoders (e.g., the fourth encoder, the fifth encoder, the sixth encoder). Since the encoders are absolute encoders, the processing device 140 may determine the values of the fourth encoder, the fifth encoder, and the sixth encoder at the target position based on the coordinates of the X-ray detector. Similarly, the processing device 140 may determine the values of the first encoder, the second encoder, and third encoder at the target position based on the coordinates of the collimator.

In some embodiments, the beam field of the collimator may be relatively large (e.g., 43*43), and X-ray detector may have enough imaging region along the Y-axis, which can cover the transverse of the object (e.g., the patient). The X-ray detector and/or the collimator may not need to move along the first axis (e.g., the Y-axis) during the X-ray imaging. Thus, the X-ray detector may not need to have the sixth encoder to detect the movement of the X-ray detector along the first axis. However, it should be noted that the X-ray detector can move along the first axis (i.g., the Y-axis) during the X-ray imaging. The sixth encoder of the X-ray detector may also need to be determined according to Equation (4). For example, the value of the sixth encoder at the first position may be determined based on the value of the sixth encoder at the second position and the distance between the first position and the second position. In some embodiments, the value of the sixth encoder at the first position may correspond to the coordinate value 0 of the Y-axis.

In some embodiments of the present disclosure, when calibrating the X-ray detector and the collimator, the processing device 140 may move the X-ray detector from the first position to the second position (a position outside the scanning table), and align the X-ray detector and the collimator at the second position without removing the bed board of the scanning table. Compared with the prior art which needs to remove the bed board of the scanning table, the calibration process may be simpler and have higher calibration efficiency.

It should be noted that the above description of the process 500 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the collimator and the X-ray detector may be aligned periodically. For example, the processing device 140 may calibrate the collimator and the X-ray detector at fixed periods. The fixed periods may be a default value or an empirical value related to the X-ray imaging system 100. The fixed periods may be a week, a month, three month, half a year, a year, two years, or the like. In some embodiments, the processing device 140 may determine whether the collimator and the X-ray detector are aligned based on images generated by the X-ray imaging system 100. For example, if the images generated by the X-ray imaging system 100 have poor quality (e.g., artifacts), the processing device 140 may determine that the collimator and the X-ray detector are unaligned. Then, the processing device 140 may perform one or more operations of the process 500 to calibrate the collimator and X-ray detector.

FIG. 6 is a schematic diagram illustrating a portion of an exemplary X-ray apparatus 600 according to some embodiments of the present disclosure. The X-ray apparatus 600 may be a decubitus imaging apparatus. The X-ray apparatus 600 may include a scanning table 610, a tray 620, and an X-ray detector 630. As shown in FIG. 6, the X-ray detector 630 is disposed on the tray 620, and the tray 620 is under the scanning table 610 and is connected to the scanning table 610. In some embodiments, the tray 620 may be connected to the scanning table 610 via a mechanical structure along a first axis (a short axis of the scanning table 610, i.e., the Y-axis of a coordinate system as shown in FIG. 6). The tray 620 may be slidably connected to the scanning table 610 along a second axis (a long axis of the scanning table 610, i.e., the X-axis of the coordinate system as shown in FIG. 6). During a calibration process, the state of the mechanical structure may be unlocked, and the connection between the tray 620 and the scanning table 610 may be loose along the first axis. Then the tray 620 may be pulled out of the scanning table 610 so that a center of an imaging region of the X-ray detector 630 may not be shielded by the scanning table 610. In some embodiments, the calibration process may be performed according to process 500 as described in FIG. 5, and the descriptions thereof are not repeated herein. During an X-ray imaging process, the state of the mechanical structure may be locked, and the tray 620 may be fixed to the scanning table 610 along the first axis. That is, the X-ray detector 630 may not move along the first axis during the X-ray imaging process. The X-ray detector 630 may move along the second axis (i.e., the X-axis) and/or the third axis (i.e., the Z-axis) during the X-ray imaging process. The coordinate of the X-ray detector 630 along the second axis may be represented by the value of a fourth encoder. The coordinate of the X-ray detector 630 along the third axis may be represented by the value of a fifth encoder. It should be noted that, in some embodiments, the tray 620 may be slidably connected to the scanning table 610 along the first axis. The X-ray detector 630 may be movable along the first axis (i.e., the Y-axis) during the X-ray imaging process. The coordinate of the X-ray detector 630 along the first axis may be represented by the value of a sixth encoder. The three encoders may be absolute encoders configured to detect the absolute coordinates of the collimator.

As shown in FIG. 6, the scanning table 610 may move along at least one of the first axis (the Y-axis), the second axis (the X-axis), or a third axis (the Z-axis). For example, before the X-ray imaging process, the scanning table 610 may need to move to a predetermined height so that the object (e.g., a patient) can conveniently lie on the scanning table 610. As another example, during the X-ray imaging process, the scanning table 610 may move along the first axis and/or the second axis to obtain the imaging of different body parts of object (e.g., the patient).

It should be noted that the above description of the X-ray apparatus 600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the tray 620 may be omitted, and the X-ray detector 630 may be directly connected to the scanning table 610.

FIG. 7 is a schematic diagram illustrating a portion of an exemplary X-ray apparatus according to some embodiments of the present disclosure. As shown in FIG. 7, the X-ray apparatus 700 may include a support component 710, an X-ray source 720, and a collimator 730. The support component 710 may include a first guide rail 712, a second guide rail 714, and a lifting frame 716. The first guide rail 712 may extend along a first axis (e.g., the Y-axis of a coordinate system as illustrated in FIG. 7, a short axis of the scanning table). The second guide rail 714 may extend along a second axis (e.g., the X-axis of the coordinate system as illustrated in FIG. 7, a long axis of the scanning table). The lifting frame 716 may have a length that is adjustable along a third axis (e.g., the Z-axis of the coordinate system as illustrated in FIG. 7, a vertical direction). The X-ray source 720 may be disposed at the lifting frame 714, and the collimator 730 may be connected with the X-ray source. Thus, the movement of the collimator 730 (or the X-ray source 720) may be achieved by the support component 710. Specifically, the movement of the collimator 730 along the first axis (e.g., the Y-axis) may be achieved by moving the lifting frame 716 along the first guide rail 712. The movement of the collimator 730 along the second axis (e.g., the X-axis) may be achieved by moving the the lifting frame 716 along the second guide rail 714. The movement of the collimator 730 along the third axis (e.g., the Z-axis) may be achieved by increasing or decreasing the length of the lifting frame 716. In some embodiments, the coordinate of the collimator 730 along the first axis may be represented by the value of a first encoder. The coordinate of the collimator 730 along the second axis may be represented by the value of a second encoder. The coordinate of the collimator 730 along the third axis may be represented by the value of a third encoder. The three encoders may be absolute encoders configured to detect the absolute coordinates of the collimator 730.

It should be noted that the above description of the X-ray apparatus 700 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, a rotating joint 740 may be disposed between the X-ray source 720 and the lifting frame 716. The X-ray source 720 and the collimator 730 may rotate on a plane that is perpendicular to the third axis (e.g., the Z-axis) via the rotating joint 740. The rotation may be detected by a first rotating encoder. The X-ray source 720 and the collimator 730 may also rotate on a plane that is perpendicular to the first axis (e.g., the Y-axis) via the rotating joint 740. The rotation may be detected by a second rotating encoder. The X-ray source 720 and the collimator 730 may also rotate on a plane that is perpendicular to the second axis (e.g., the X-axis) via the rotating joint 740. The rotation may be detected by a third rotating encoder. In some embodiments, the rotating encoders may absolute encoders configured to detect the absolute angles of the collimator 730. Alternatively, the rotating encoders may be relative encoders configured to detect angular variations of the collimator 730.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for calibrating an X-ray apparatus, which includes an X-ray detector and a collimator, comprising:
    moving the X-ray detector from a first position to a second position, wherein the first position is under a scanning table, and the second position is outside the scanning table;
    aligning the collimator with the X-ray detector at the second position;
    determining one or more parameters, wherein the one or more parameters include at least one of a distance between the first position and the second position, or a first value of a first encoder of the collimator when the collimator is aligned with the X-ray detector at the second position; and
    determining a second value of the first encoder based at least in part on the distance between the first position and the second position and the first value of the first encoder so that the collimator is aligned with the X-ray detector at the first position based on the second value of the first encoder.

2. The method of claim 1, wherein the aligning the collimator with the X-ray detector comprises:
    aligning a center of a beam field of the collimator with a center of an imaging region of the X-ray detector at the second position.

3. The method of claim 1, wherein the first position has a first reference coordinate along a first axis of a coordinate system and/or a second reference coordinate along a second axis of the coordinate system.

4. The method of claim 1, further comprising:
    moving the X-ray detector back to the first position; and
    moving the collimator based on the second value of the first encoder so that the collimator is aligned with the X-ray detector at the first position.

5. The method of claim 4, wherein the first encoder detects a movement of the collimator along the first axis of the coordinate system, and the collimator further includes at least one of a second encoder and a third encoder,
    wherein the second encoder detects a movement of the collimator along a second axis of the coordinate system, and the third encoder detects a movement of the collimator along a third axis of the coordinate system.

6. The method of claim 5, wherein the one or more parameters further includes a value of the second encoder and a value of the third encoder when the collimator is aligned with the X-ray detector at the second position, and the moving the collimator so that the collimator is aligned with the X-ray detector at the first position further comprises:
    moving the collimator based on the second value of the first encoder, the value of the second encoder, and the value of the third encoder.

7. The method of claim 1, wherein the X-ray detector includes at least one of a fourth encoder and a fifth encoder, wherein the fourth encoder detects a movement of the X-ray detector along a second axis of the coordinate system, and the fifth encoder detects a movement of the X-ray detector along a third axis of the coordinate system.

8. The method of claim 7, wherein the one or more parameters further includes a value of the fourth encoder and a value of the fifth encoder when the X-ray detector is at the second position, wherein the value of the fourth encoder corresponds to a second reference coordinate of the X-ray detector along the second axis, and the value of the fifth encoder corresponds to a third reference coordinate of the X-ray detector along the third axis.

9. The method of claim 7, wherein the X-ray detector further includes a sixth encoder, wherein the sixth encoder detects a movement of the X-ray detector along the first axis of the coordinate system and detects a coordinate of the second position of the X-ray detector along the first axis.

10. The method of claim 1, wherein the determining a second value of the first encoder comprises:
determining the second value of the first encoder based on the first value of the first encoder, a coefficient of the first encoder, and the distance between the first position and the second position.

11. The method of claim 1, wherein the collimator and the X-ray detector are aligned periodically.

12. A system for calibrating an X-ray apparatus, which includes an X-ray detector and a collimator, comprising:
at least one storage device including a set of instructions;
at least one processor in communication with the at least one storage device, wherein when executing the set of instructions, the at least one processor is configured to cause the system to:
move the X-ray detector from a first position to a second position, wherein the first position is under a scanning table, and the second position is outside the scanning table;
align the collimator with the X-ray detector at the second position;
determine one or more parameters, wherein the one or more parameters include at least one of a distance between the first position and the second position, or a first value of a first encoder of the collimator when the collimator is aligned with the X-ray detector at the second position; and
determine a second value of the first encoder based at least in part on the distance between the first position and the second position and the first value of the first encoder so that the collimator is aligned with the X-ray detector at the first position based on the second value of the first encoder.

13. The system of claim 12, wherein to align the collimator with the X-ray detector, the at least one processor is further configured to cause the system to:
align a center of a beam field of the collimator with a center of an imaging region of the X-ray detector at the second position.

14. The system of claim 12, wherein the first position has a first reference coordinate along a first axis of a coordinate system and/or a second reference coordinate along a second axis of the coordinate system.

15. The system of claim 12, the at least one processor is further configured to cause the system to:
move the X-ray detector back to the first position; and
move the collimator based on the second value of the first encoder so that the collimator is aligned with the X-ray detector at the first position.

16. The system of claim 15, wherein the first encoder detects a movement of the collimator along the first axis of the coordinate system, and the collimator further includes at least one of a second encoder and a third encoder, wherein the second encoder detects a movement of the collimator along a second axis of the coordinate system, and the third encoder detects a movement of the collimator along a third axis of the coordinate system.

17. The system of claim 16, wherein the one or more parameters further includes a value of the second encoder and a value of the third encoder when the collimator is aligned with the X-ray detector at the second position, and to move the collimator so that the collimator is aligned with the X-ray detector at the first position, the at least one processor is further configured to cause the system to:
move the collimator based on the second value of the first encoder, the value of the second encoder, and the value of the third encoder.

18. The system of claim 12, wherein the X-ray detector includes at least one of a fourth encoder and a fifth encoder, wherein the fourth encoder detects a movement of the X-ray detector along a second axis of the coordinate system, and the fifth encoder detects a movement of the X-ray detector along a third axis of the coordinate system.

19. The system of claim 12, wherein to determine a second value of the first encoder, the at least one processor is configured to cause the system to:
determine the second value of the first encoder based on the first value of the first encoder, a coefficient of the first encoder, and the distance between the first position and the second position.

20. A non-transitory computer-readable medium, comprising at least one set of instructions, wherein when executed by at least one processor of a computing device, the at least one set of instructions cause the at least one processor to effectuate a method comprising:
moving the X-ray detector from a first position to a second position, wherein the first position is under a scanning table, and the second position is outside the scanning table;
aligning the collimator with the X-ray detector at the second position;
determining one or more parameters, wherein the one or more parameters include at least one of a distance between the first position and the second position, or a first value of a first encoder of the collimator when the collimator is aligned with the X-ray detector at the second position; and
determining a second value of the first encoder based at least in part on the distance between the first position and the second position and the first value of the first encoder so that the collimator is aligned with the X-ray detector at the first position based on the second value of the first encoder.

* * * * *